(12) United States Patent
Hallbeck et al.

(10) Patent No.: US 11,672,544 B2
(45) Date of Patent: Jun. 13, 2023

(54) TOURNIQUET TRAINING DEVICE

(71) Applicant: Mayo Foundation for Medical Education and Research, Rochester, MN (US)

(72) Inventors: M. Susan Hallbeck, Rochester, MN (US); Bethany R. Lowndes, Gretna, NE (US); Carl-Oscar Jonson, Linköping (SE); Erik Prytz, Linköping (SE); Amro M. Abdelrahman, Rochester, MN (US); Katherine E. Law, Rochester, MN (US); Renaldo C. Blocker, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 658 days.

(21) Appl. No.: 16/636,408

(22) PCT Filed: Aug. 3, 2018

(86) PCT No.: PCT/US2018/045164
§ 371 (c)(1),
(2) Date: Feb. 4, 2020

(87) PCT Pub. No.: WO2019/028348
PCT Pub. Date: Feb. 7, 2019

(65) Prior Publication Data
US 2020/0170649 A1 Jun. 4, 2020

Related U.S. Application Data

(60) Provisional application No. 62/541,426, filed on Aug. 4, 2017.

(51) Int. Cl.
*A61B 17/135* (2006.01)
*A61B 5/00* (2006.01)
*A61B 17/00* (2006.01)

(52) U.S. Cl.
CPC .......... *A61B 17/135* (2013.01); *A61B 5/0053* (2013.01); *A61B 5/4848* (2013.01);
(Continued)

(58) Field of Classification Search
CPC ..... A61B 5/0053; A61B 5/026; A61B 5/4848; A61B 5/6824; A61B 5/6828;
(Continued)

(56) References Cited

U.S. PATENT DOCUMENTS

| 6,210,423 B1 * | 4/2001 | Kim | A61F 5/34 |
| | | | 128/898 |
| 7,909,849 B2 | 3/2011 | McEwen | |

(Continued)

OTHER PUBLICATIONS

International Preliminary Report on Patentability in International Application No. PCT/US2018/045164 dated Feb. 13, 2020, 7 pages.
(Continued)

*Primary Examiner* — Jocelin C Tanner
(74) *Attorney, Agent, or Firm* — Fish & Richardson P.C.

(57) ABSTRACT

This document provides methods and materials for improving the training on the use of tourniquets. For example, methods and devices for confirming the proper pressure of a tourniquet using a tourniquet training device are provided.

27 Claims, 2 Drawing Sheets

(52) U.S. Cl.
CPC ............... *A61B 2017/00119* (2013.01); *A61B 2017/00707* (2013.01); *A61B 2505/01* (2013.01)

(58) Field of Classification Search
CPC ........ A61B 17/135; A61B 2017/00119; A61B 2017/00707; G09B 23/28; G09B 23/30
See application file for complete search history.

(56) References Cited

U.S. PATENT DOCUMENTS

| | | | |
|---|---|---|---|
| 8,047,850 B2 | 11/2011 | Esposito et al. | |
| 8,083,763 B2* | 12/2011 | McEwen | A61B 17/1355 73/40 |
| 8,221,129 B2 | 7/2012 | Parry et al. | |
| 8,764,685 B2 | 7/2014 | Casey | |
| 2006/0070183 A1 | 4/2006 | Ekins | |
| 2006/0226305 A1 | 10/2006 | Sheybani | |
| 2008/0177159 A1 | 7/2008 | Gavriely | |
| 2009/0005804 A1* | 1/2009 | Esposito | A61B 17/1322 434/262 |
| 2010/0234877 A1 | 9/2010 | Pienkowski et al. | |
| 2013/0309643 A1* | 11/2013 | Segall | G09B 23/303 434/268 |
| 2018/0190142 A1* | 7/2018 | Quail | G09B 23/28 |

OTHER PUBLICATIONS

International Search Report & Written Opinion in International Application No. PCT/US2018/045164 dated Oct. 24, 2018, 14 pages.

* cited by examiner

TOURNIQUET TRAINING DEVICE

CROSS-REFERENCE TO RELATED APPLICATIONS

This application is a National Stage application under 35 U.S.C. § 371 of International Application No. PCT/US2018/045164, having an International Filing Date of Aug. 3, 2018, which claims priority to U.S. Application Ser. No. 62/541,426, filed on Aug. 4, 2017. The disclosure of the prior application is considered part of the disclosure of this application, and is incorporated in its entirety into this application.

BACKGROUND

1. Technical Field

This document relates to methods and materials for improving the use of tourniquets. For example, this document relates to methods and devices for confirming the proper pressure of a tourniquet using a tourniquet training device.

2. Background Information

Exsanguination, also known as bleeding to death, is a risk faced by individuals involved in accidents, combat wounds, or other forms of severe trauma. Bleeding to death can be caused by both internal and external wounds; however, exsanguination by external wounds can be prevented by applying a tourniquet to an injured individual closer to the heart than the wound.

Tourniquets are used for stopping or reducing blood flow through a vein or artery by applying pressure circumferentially around a bleeding extremity. The pressure experienced by the individual transfers through their skin to the tissues of the extremity, causing compression of the walls of arterial vessels and restricting blood flow. While there are tourniquets available for purchase that include straps, buckles, hook and loop connections, or other means to secure the tourniquet around the extremity, everyday articles (e.g., belts, clothing, bandanas, ties, or rope) can also be fashioned into a tourniquet.

When using a tourniquet, it is important to apply pressure sufficient to substantially stop blood flow, while avoiding unnecessary additional pressure. The tourniquet can only be removed once the wound has been dressed appropriately to limit blood flow or other medical procedures have occurred that eliminate or reduce the risk of exsanguination.

SUMMARY

This document provides methods and materials for improving the use of tourniquets. For example, this document provides methods and materials for confirming the proper pressure of a tourniquet using a tourniquet training device. In some cases, a tourniquet training device provided herein can be an inexpensive, easy to use, tourniquet training device that does not put an individual at risk of excessive pressure on an extremity that could cause an excessive reduction in blood flow, or blood flow to substantially stop, which could lead to adverse events such as pain, bruising, or necrosis (i.e., death of most or all of the cells in an organ or tissue due to failure of the blood supply). The device is used for training for individuals to apply the tourniquet and supports the "gold standard" of buddy training, increases effective hands-on practice time, and allows training of people unwilling or unable to accept the pain from having a tourniquet tightened on their extremity (e.g., children, elderly, or injured persons) or with a standardized patient.

In general, one aspect of this document features a tourniquet training device. The tourniquet training device can include a sleeve (e.g., a rigid sleeve) or a rigid component and/or layer that is placed over an extremity (e.g., arm or leg) of a person who is using the training device or who is assisting another person using the training device. The tourniquet training device can be secured on the extremity via a layer of compressible material, or one or more air bladders on an internal portion of the sleeve that would interact with skin of a subject to create a secure fit. The tourniquet training device can include a compressible material on an external portion of the sleeve. The compressible material on the external portion of the sleeve can serve as an artificial extremity designed to receive pressure from a test tourniquet. The sleeve (e.g., rigid sleeve) underneath can be designed to minimize compression applied to the person wearing the device by a test tourniquet. This minimized compression will aid in maintaining the location of the tourniquet training device on the trainer, "buddy," or standardized patient, with minimal discomfort when compared to a tourniquet applied directly to the trainer, "buddy," or standardized patient.

In some cases, the tourniquet training device can include a sensor to measure the pressure applied by a test tourniquet during training, or a tube (e.g., a fluid filled tube) with a sensor to measure flow within the tube as an indicator of the pressure applied by the test tourniquet during training, or both. In some cases, the sensor and/or tube and sensor can be located within the compressible material. In some cases, when a tube is included in the tourniquet training device, the tube can be designed to represent a venous or arterial vessel, and the tube can be filled with a fluid designed to represent blood (e.g., with similar properties to blood). In such cases, a pump can be included to pump the fluid through the tube. In some cases, pressure data and/or flow data obtained from the sensor(s) can be used to determine whether or not the amount of pressure applied by a test tourniquet is effective. In some cases, an indicator element can be directly attached to the tourniquet training device and designed to provide an indication of the tourniquet effectiveness. In some cases, a tourniquet training device can be designed to send a signal to another device (e.g., a smartphone or computer) to alert the user and/or others about tourniquet effectiveness.

In another aspect, this document features a method for confirming a proper pressure of a test tourniquet. In some cases, a tourniquet training device provided herein can include an electronic sensor (e.g., a force sensor, flow sensor, or pressure sensor). In some cases, a force sensor can be embedded in the external compressible material and provide pressure data based on the amount of pressure applied by the test tourniquet. In some cases, a flow sensor can be embedded in the external compressible material to provide flow data of the flow of a liquid through a tube provided within the external compressible material. The effectiveness of tourniquet pressure can be communicated to a user and others via sound, light, vibration, and/or a display. Features of the tube(s), sensor(s), and/or indicator(s) can be dynamic, such that they can be replaced or adjusted to require different amounts of pressure to achieve a successful indication of proper pressure. For example, a tube, a pressure sensor(s), or indicator(s) can be set to simulate a smaller body type requiring less pressure for successful application, and then the tube can be replaced, or the sensor(s) or indicator(s) can be adjusted, for a larger body type requiring more pressure for successful application. Other replacements or adjustments can be used to simulate pressures for differences in gender, age, body type, or health of an individual.

In another aspect, this document features a tourniquet training device. The tourniquet training device comprises (or consists essentially of) a sleeve defining an inner lumen configured to receive an arm or leg of a human, and an external compressible member at least partially surrounding an exterior of the sleeve, where pressure applied to the external compressible member via a tourniquet in an amount that reduces blood flow of a comparable arm or leg in the absence of the tourniquet training device does not stop blood flow when the arm or leg is positioned within the sleeve. The tourniquet training device can include a sensor embedded in the external compressible member. The sensor can be a force sensor. The tourniquet training device can include an indicator configured to indicate a tourniquet effectiveness based on data received from the sensor. The indicator can be a light, a sound, a vibration, and/or a display. The tourniquet training device can include a tube coupled to a fluid flow device, and the tube and the fluid flow device can be embedded within the external compressible member. The tube can be filled with a fluid, and the sensor can be coupled to the tube. The sensor can be a flow sensor or a pressure sensor. The tube can be removable from the external compressible member. The internal compressible member can be an air bladder. The sleeve can be rigid. The tourniquet training device can include an internal compressible member located within the sleeve, and the internal compressible member can be located between the sleeve and the arm or leg when the arm or leg is positioned within the sleeve.

In another aspect, this document features a method of using a tourniquet training device. The tourniquet training device comprises (or consists essentially of) a sleeve defining an inner lumen configured to receive an arm or leg of a human, an external compressible member at least partially surrounding an exterior of the sleeve, and a sensor for measuring pressure applied to the external compressible member. The method comprises (or consists essentially of) (a) positioning the arm or the leg within the inner lumen, (b) applying pressure via a tourniquet to the external compressible member, and (c) receiving an indication of tourniquet effectiveness from the tourniquet training device or a device in communication with the tourniquet training device, where the indication of tourniquet effectiveness is based on force data obtained from the sensor, or data corresponding to force data. In some cases, pressure applied to the external compressible member via the tourniquet in an amount that stops, or reduces, blood flow of a comparable arm or leg in the absence of the tourniquet training device does not stop blood flow when the arm or leg is positioned within the sleeve. The sensor can be a force sensor. The tourniquet training device can comprise an indicator configured to indicate a tourniquet effectiveness based on data received from the sensor. The indicator can be a light, a sound, a vibration, and/or a display. The tourniquet training device can comprise a tube coupled to a fluid flow device, and the tube and the fluid flow device can be embedded within the external compressible member. The tube can be filled with a fluid, and the sensor can be coupled to the tube. The sensor can be a flow sensor or a pressure sensor. The tube can be removable from the external compressible member. The internal compressible member can be an air bladder. The sleeve can be rigid. The tourniquet training device can include an internal compressible member located within the sleeve, and the internal compressible member can be located between the sleeve and the arm or leg when the arm or leg are positioned within the sleeve. The method can include adjusting the pressure of the tourniquet based on the indication of tourniquet effectiveness. The method can comprise receiving a second indication of tourniquet effectiveness via the indicator.

Particular embodiments of the subject matter described in this document can be implemented to realize one or more of the following advantages. The extremity of the subject wearing the training device can experience little to no pressure due to the external compressible material serving as the artificial extremity that receives pressure from a test tourniquet and the sleeve (e.g., rigid sleeve) that limits the amount of compression the subject feels. This is advantageous as it minimizes risks of reducing or stopping blood flow of the subject wearing the training device. The indicator is advantageous as a user and others can receive instant feedback regarding proper pressure of a test tourniquet, which can increase correct tourniquet use when applying a tourniquet in actual field use. Further, some embodiments provided herein can provide portable, easy to use, inexpensive, and dynamic tourniquet training devices.

Unless otherwise defined, all technical and scientific terms used herein have the same meaning as commonly understood by one of ordinary skill in the art to which this document pertains. Although methods and materials similar or equivalent to those described herein can be used to practice the disclosed device, suitable methods and materials are described herein. All publications, patent applications, patents, and other references mentioned herein are incorporated by reference in their entirety. In case of conflict, the present specification, including definitions, will control. In addition, the materials, method and examples are illustrative only and not intended to be limiting.

The details of one or more embodiments of the document are set forth in the accompanying drawings and the description below. Other features, objects, and advantages of the document will be apparent from the description and drawings, and from the claims.

DESCRIPTION OF DRAWINGS

Like reference numbers represent corresponding parts throughout.

DETAILED DESCRIPTION

This document provides methods and materials for improving the use of tourniquets and training tourniquet use with humans without pain or blood flow reduction. For example, this document provides methods and materials for confirming the proper pressure of a test tourniquet using a tourniquet training device.

To prevent an individual from bleeding to death, tourniquets are used to reduce or stop blood flow through an artery by applying pressure circumferentially around an extremity.

The pressure experienced by the individual transfers through their skin to the tissues of the extremity, causing compression of the walls of arterial vessels and limiting or restricting blood flow. Training for proper tourniquet placement and pressure applied, however, can be limited due to high expenses associated with current training devices.

This document provides a tourniquet training device such that an extremity (e.g., an arm or leg) of a subject wearing the training device and receiving a test tourniquet experiences little (e.g., enough to hold up the sleeve) to no pressure on that extremity. This is advantageous as it minimizes risks of reducing or stopping blood flow during training. In addition, a user (i.e., an individual placing the tourniquet) and others can receive feedback (e.g., instant feedback) regarding proper pressure of a test tourniquet when using a tourniquet training device provided herein, which can increase correct tourniquet use when applying a tourniquet in real life. In some cases, a subject wearing a training device also can be a user placing the tourniquet. In some cases, a subject wearing the training device can be different than a user placing the test tourniquet. In some cases, a training device provided herein can be a portable, easy to use, inexpensive, and dynamic tourniquet training device.

Figure 1:
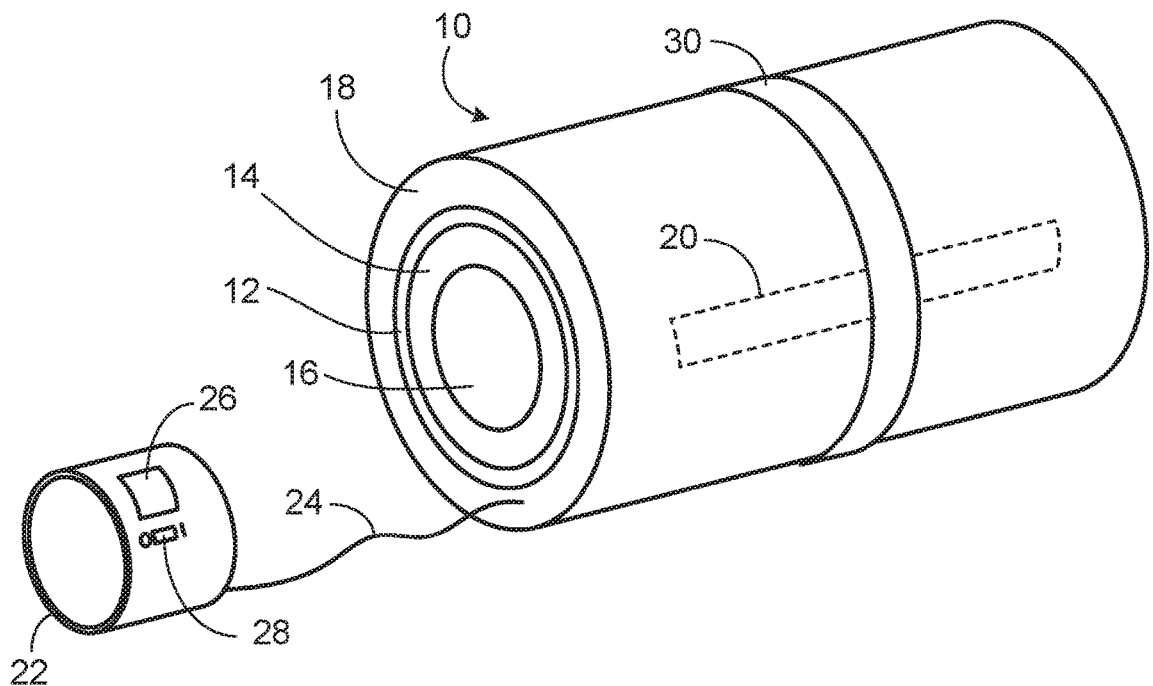
FIG. 1 is a perspective view of a tourniquet training device in accordance with some embodiments provided herein.

Referring to FIG. 1, a tourniquet training device 10 can include a sleeve 12. Sleeve 12 can include an internal compressible member 14, an external compressible member 18, and a sensor 20. In some cases, tourniquet training device 10 can include a test tourniquet 30. In some cases, tourniquet training device 10 can include an extremity cuff 22. Extremity cuff 22 can include an indicator 26 to provide feedback regarding effectiveness of test tourniquet 30 or any other tourniquet applied to tourniquet training device 10.

Sleeve 12 can define an internal chamber that houses internal compressible member 14. Sleeve 12 can be made of a substantially rigid material, such as plastic or metal, to minimize or prevent compression of sleeve 12 when pressure is applied via test tourniquet 30 or any other tourniquet. In some cases, sleeve 12 can be cylindrical with a substantially uniform diameter along the length of sleeve 12. In some cases, sleeve 12 may have a diameter that varies along the length of sleeve 12. For example, the diameter of sleeve 12 can decrease at a more distal end of sleeve 12, such that sleeve 12 has a conical shape that aligns more with a shape of an extremity (e.g., arm or leg) of a person wearing tourniquet training device 10. In some cases, sleeve 12 can have a length from about 10 cm to about 40 cm. In some cases, sleeve 12 can have a diameter from about 20 cm to about 60 cm. In some cases, tourniquet training device 10 can be available in multiple sizes such that an appropriate size can be selected based on the size of the subject (e.g., to accommodate a child vs a bodybuilder).

Internal compressible member 14 can be enclosed within the internal chamber defined by sleeve 12 and the internal compressible member 14 can define an internal chamber 16 that receives an extremity (e.g., an arm or leg) of a subject (e.g., a person). In some cases, internal compressible member 14 can be coupled to sleeve 12. Internal compressible member 14 can be made of a compressible material (e.g., neoprene, upholstery foam, or rubber) or one or more air bladders such that when sleeve 12 is placed on an extremity, internal compressible member 14 interacts with the extremity to create secure coupling between sleeve 12 and the extremity. In some cases, internal compressible member 14 can provide additional comfort to the wearer when wearing sleeve 12. In some cases, a length of internal compressible material 14 can be substantially similar to the length of sleeve 12. In some cases, the length of internal compressible material 14 can be different (e.g., longer or shorter) than the length of sleeve 12. For example, the length of internal compressible material 14 can be longer than sleeve 12 to limit contact between sleeve 12 and the extremity of the subject. Such a design can increase comfort of a subject by reducing the risk of a hard edge of sleeve 14 contacting the extremity of the subject. In some cases, internal chamber 16 can be cylindrical with a substantially uniform diameter along a length of internal chamber 16. In some cases, internal chamber 16 can have a diameter that varies along the length of internal chamber 16. For example, the diameter of an internal chamber can decrease at a more distal end of the internal chamber, such that the internal chamber has a conical shape that aligns more with a shape of an extremity (e.g., an arm or leg) of a user (e.g., a person wearing the tourniquet training device 10).

In some cases, internal compressible member 14 can include only a compressible material. In some cases, internal compressible member 14 can include compressible material and a liner (not shown) that can cover the compressible material to interact with an extremity. In some cases, the liner can have a different coefficient of friction than the compressible material to increase or decrease the friction of internal compressible member 14. In some cases, the liner can provide a surface that can be cleaned easily between uses of sleeve 12. In some cases, the liner can be permanently coupled to the compressible material and/or sleeve 12. In some cases, the liner can be removably coupled (e.g., via snaps, buttons, or hook and loop connectors) to the compressible material and/or sleeve 12.

External compressible member 18 can partially or completely surround sleeve 12 and can define an external surface that can interact with test tourniquet 30. In some cases, external compressible member 18 can be coupled to sleeve 12. External compressible member 18 can be made of a compressible material (e.g., upholstery, foam, or ballistics gel). In some cases, a length of external compressible material 18 can be substantially similar to the length of sleeve 12. In some cases, the length of external compressible material 18 can be different (e.g., longer or shorter) than the length of sleeve 12. In some cases, the compressible material of internal compressible member 14 and external compressible member 18 can be the same compressible material. In some cases, the compressible material of internal compressible member 14 and external compressible member 18 can be different compressible materials. In some cases, internal compressible member 14 can be coupled to external compressible member 18 such that sleeve 12 is not exposed.

In some cases, external compressible member 18 can be cylindrical with a substantially uniform diameter along a length of external compressible member 18. In some cases, external compressible member 18 can have a diameter that varies along the length of external compressible member 18. For example, the diameter of external compressible member 18 can decrease at a more distal end of external compressible member 18, such that external compressible member 18 can have a conical shape that aligns more with a shape of an extremity (e.g., arm or leg) of a user (e.g., a person wearing tourniquet training device 10). In some cases, external compressible member 18 can have a diameter that various to replicate anatomical features of a person (e.g., muscles and/or tissue).

In some cases, external compressible member 18 can include only a compressible material. In some cases, external compressible member 18 can include compressible material and a cover (not shown) that can partially or completely surround the compressible material to interact with test tourniquet 30 and the user (e.g., a person applying test tourniquet 30). In some cases, external compressible member 18 can have an appearance of skin (e.g., color and/or texture). In some cases, the cover can provide characteristics similar to those of human skin (e.g., coefficient of friction and/or malleability). In some cases, the cover can have a different coefficient of friction than the compressible material to increase or decrease the friction of external compressible member 18. In some cases, the cover can provide a surface that can be cleaned easily between uses of sleeve 12. In some cases, the cover can be permanently coupled to the compressible material and/or sleeve 12. In some cases, the cover can be removably coupled (e.g., via snaps, buttons, or hook and loop connectors) to external compressible member 18 and/or sleeve 12. In some cases, when the cover is partially or fully removed, the user can gain access to sensor(s) 20.

In some cases, test tourniquet 30 can be included with tourniquet training device 10. In some cases, pre-provided test tourniquet 30 can be removed or not provided such that a user must fashion or obtain a tourniquet. For example, a user can fashion a tourniquet from everyday articles (e.g., belts, bandanas, clothing, or rope), or taught how to fashion such a tourniquet. In some cases, test tourniquet 30 can include a securing component (not shown) that can secure test tourniquet 30 around external compressible member 18 of sleeve 12. In some cases, the securing component can be straps, buckles, ratchets, snaps, buttons, and/or hook and loop connectors. In some cases, test tourniquet 30 can be secured by tying two ends of test tourniquet 30 together.

Sensor(s) 20 can be embedded in external compressible member 18 such that sensor(s) 20 can experience forces caused by applying test tourniquet 30 or any other tourniquet. In some cases, sensor(s) 20 can be a force sensor(s). In some cases, such as shown in FIG. 1, sensor(s) 20 extends a length of sleeve 12 such that sensor 20 can collect force information regardless of a location of test tourniquet 30. In some cases, sensor(s) 20 can be located circumferentially around sleeve 12. In some cases, sensor(s) 20 can be located in an area of external compressible member 18 that can coincide with a location of arterial or venous vessel of human anatomy. In some cases, tourniquet training device 10 can include multiple sensors 20 (e.g., two, three, four, five, or more sensors) embedded in external compressible member 18. In some cases, sensor 20 can be dynamically changed to simulate bleeding out or other habitus features of a body that can vary based on an individual or a severity of a wound. In some cases, sensor 20 can be designed to communicate with extremity cuff 22, a separate device (e.g., a smartphone), or both. For example, sensor 20 can communicate with a mobile device (e.g., cellular device, tablet, PDA, or smartphone) in addition to, or instead of, communicating with extremity cuff 22. Sensor 20 can communicate with extremity cuff 22 and/or additional devices via a connection 24.

In some cases, connection 24 can be a wired connection (as shown in FIG. 1). In some cases, connection 24 can be a wireless connection (e.g., Bluetooth, Wi-Fi, cellular networks, 3G; LTE, RF, and/or Zigbee). In some cases, sensor 20 can communicate via both wired and wireless connections 24. In some cases, different information can be transmitted based on the type of connection 24 being used.

Extremity cuff 22 can define an internal chamber that receives a distal extremity (e.g., wrist or ankle) of a user (e.g., a person wearing tourniquet training device 10). In some cases, extremity cuff 22 can be made of a substantially stretchable or flexible material (e.g., elastic, neoprene, or polyester), such that the user can slide extremity cuff 22 into place and extremity cuff 22 can be secured due to a stretchable configuration of extremity cuff 22. In some cases, extremity cuff 22 can include a securing component (not shown) to secure extremity cuff 22 around the distal extremity of the user. In some cases, the securing component can be straps, hooks, buckles, ratchets, snaps, buttons, or hook and loop connectors. In some cases, extremity cuff 22 can have a width from about 3 cm to about 10 cm. In some cases, extremity cuff 22 can have a diameter that can vary from about 5 cm to about 30 cm, from about 10 cm to about 25 cm, from about 5 cm to about 10 cm, and/or from about 10 cm to about 30 cm. Extremity cuff 22 can include circuitry that can enable communication between sensor 20 and extremity cuff 22, specifically between sensor 20 and indicator 26. In some cases, extremity cuff 22 can include a power switch or button 28 that can enable the circuitry of extremity cuff 22 to be enabled or disabled. In some cases, power switch or button 28 can only control circuity of extremity cuff 22. In some cases, power switch or button 28 can control circuitry of extremity cuff 22 and circuity located on sleeve 12.

Indicator 26 can provide an indication of tourniquet effectiveness to the subject, the user, and others by simulating a distal pulse based on the forces sensed by sensor 20 due to application of test tourniquet 30 or any other tourniquet. In some cases, indicator 26 can provide immediate feedback based on sensor(s) 20. In some cases, the user can initiate feedback from indicator 26. For example, once the user has applied test tourniquet 30 and is ready for feedback, the user can press a button, flip a switch, or turn on indicator 26. In some cases, there can be a delay between turning on extremity cuff 22 and activating indicator 26. The user can turn extremity cuff 22 on and apply test tourniquet 30 or any other tourniquet around external compressible member 18 within a designated amount of time before receiving feedback from indicator 26. This can be beneficial to test users in a more realistic environment where the user may not receive constant, and accurate, updates of tourniquet effectiveness.

In some cases, indicator 26 can use a combination of thresholds to define different ranges of forces (e.g., not enough force, adequate force, or too much force) that can cause changes to indicator 26. In some cases, indicator 26 can be a light (e.g., LED, florescent, incandescent, halogen, or tungsten), or a combination of lights. In some cases, indicator 26 can change a brightness of the light as the force detected by sensor(s) 20 changes. In some cases, indicator 26 can change color to indicate the force detected by sensor(s) 20. For example, a yellow light can indicate that a tourniquet is not applying enough force to sensor(s) 20, a green light can indicate that a tourniquet is applying adequate force to sensor(s) 20, and a red light can indicate that a tourniquet is applying too much force to sensor(s) 20. In some cases, indicator 26 can be a light bar, such that the light bar can illuminate distinct lights, or a plurality of lights, to coincide with the simulated pulse based on the force detected by sensor(s) 20. In some cases, the light bar can illuminate distinct lights, or a plurality of lights, to coincide with an amount of force applied to sensor(s) 20.

In some cases, indicator 26 can provide haptic feedback (e.g., vibration). For example, indicator 26 can change an intensity of the haptic feedback as the force measured by sensor 20 changes. As another example, indicator 26 can provide a short burst of haptic feedback when a threshold is crossed (e.g., from too little force to adequate force, or from adequate force to too much force). In some cases, indicator 26 can provide different haptic patterns (e.g., bursts of vibration at different speeds or intensities) when various thresholds are crossed or when the force is in a designated force range.

In some cases, indicator 26 can be a speaker. In some cases, a volume of the speaker can change as the force from sensor 20 changes. In some cases, indicator 26 can provide a short sound when a threshold is crossed (e.g., from too little force to adequate force, or from adequate force to too much force). In some cases, indicator 26 can provide different sounds when various thresholds are crossed or when the force is in a designated force range.

In some cases, indicator 26 can be digital numbers indicating a simulated pulse based on the force detected by sensor(s) 20. In some cases, a user can select the type of indicator 26. In some cases, a combination of indicators 26 can be used.

In some cases, indicator 26 can be on a mobile device. In some cases, the mobile device can be able to show a progression (e.g., a graph or a table) of the simulated pulse. In some cases, indicator 26 on the mobile device can have similar capabilities or features as described herein with regard to indicator 26 of extremity cuff 22.

Figure 2:
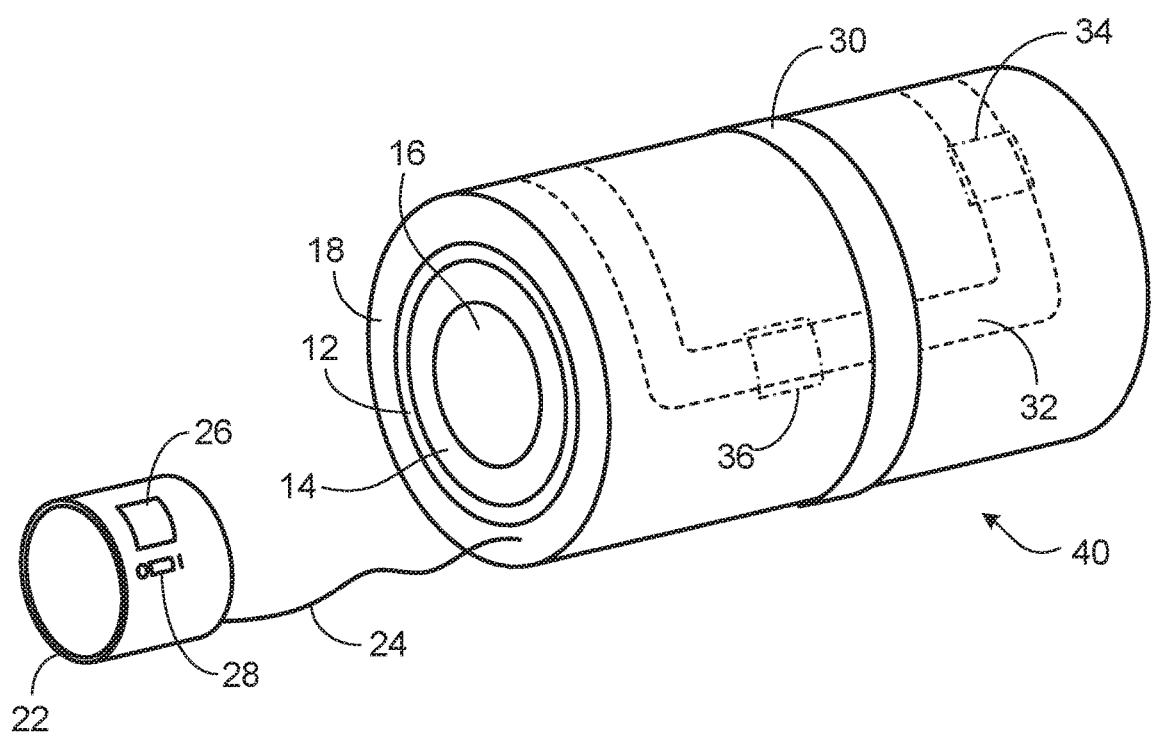
FIG. 2 is a perspective view of a second tourniquet training device in accordance with some embodiments provided herein.

Referring to FIG. 2, a tourniquet training device 40 can include a sleeve 12. Sleeve 12 can include an internal compressible member 14 and an external compressible member 18. In some cases, tourniquet training device 40 can include a test tourniquet 30 or can lack test tourniquet 30. In some cases, tourniquet training device 40 can include an extremity cuff 22. Extremity cuff 22 can include an indicator 26 to provide feedback regarding the effectiveness of test tourniquet 30 or any other tourniquet applied to tourniquet training device 40. Sleeve 12, internal compressible member 14, external compressible member 18, extremity cuff 22, indicator 26, power switch or button 28, and connection 24 of tourniquet training device 40 can be substantially similar to the corresponding components of tourniquet training device 10 of FIG. 1.

External compressible member 18 of tourniquet training device 40 can house a tube 32 filled with a fluid. In some cases, tube 32 can be exclusively located in external compressible member 18 and can create a complete flow path. In some cases, tube 32 can extend out of external compressible member 18, such that a user can see fluid flowing through tube 32. In some cases, tube 32 can run along an end of external compressible member 18, such that tube 32 is visible, but still embedded in external compressible member 18. In some cases, tube 32 can extend to extremity cuff 22 or can partially extend to extremity cuff 22. Tube 32 can be sized and shaped to replicate arterial and/or venous blood vessels. Tube 32 can be coupled to a fluid flow device 34 that generates fluid flow to replicate the flowing of blood through tube 32. In some cases, the fluid can have a consistency and/or color similar to that of blood. In some cases, a user can remove tube 32 from external compressible member 18 and insert another tube 32, which can have a different rigidity, such that a different amount of force would need to be applied with test tourniquet 30 or any other tourniquet to achieve a similar level of effectiveness.

External compressible member 18 can include a sensor(s) 36 coupled to tube 32. In some cases, sensor(s) 36 can be a flow sensor. In some cases, sensor(s) 36 can be a pressure sensor. Communication between sensor(s) 36 and extremity cuff 22 (e.g., indicator 26) can be substantially similar to the communication between sensor(s) 20 and extremity cuff 22. Further, operation of indicator 26 can be substantially similar or identical to that of indicator 26, as described with respect to FIG. 1.

Figure 3:
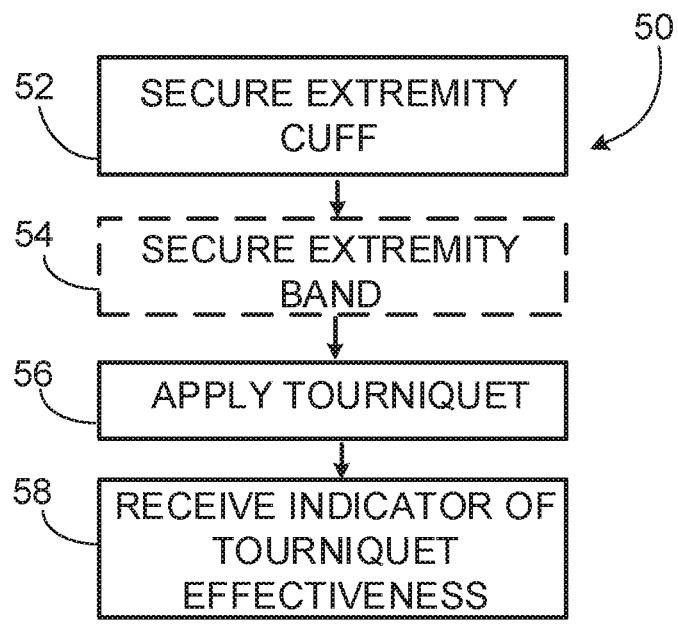
FIG. 3 is a method of using a tourniquet training device in accordance with some embodiments provided herein.

Referring to FIG. 3, a method 50 of using tourniquet training device 10 or tourniquet training device 40 is shown. A user can secure sleeve 12 on an extremity of a subject at 52. The extremity can go into internal chamber 16 and can be secured in place via internal compressible member 14. In some cases, the user can secure extremity cuff 22 at 54. Extremity cuff 22 can be secured to a distal end of the extremity of the subject. Extremity cuff 22 can be secured automatically due to a stretchable material of extremity cuff 22 or by using a securing component, as described herein. The user can apply test tourniquet 30 or any other tourniquet at 56. Test tourniquet 30 (or any other tourniquet) can be applied to external compressible member 18 and can be tightened to a desired level of compression. The user can receive an indicator of tourniquet effectiveness at 58. The indicator of tourniquet effectiveness can be provided via indicator 26, which can be located on extremity cuff 22, a mobile device, or a combination thereof.

Figure 4:
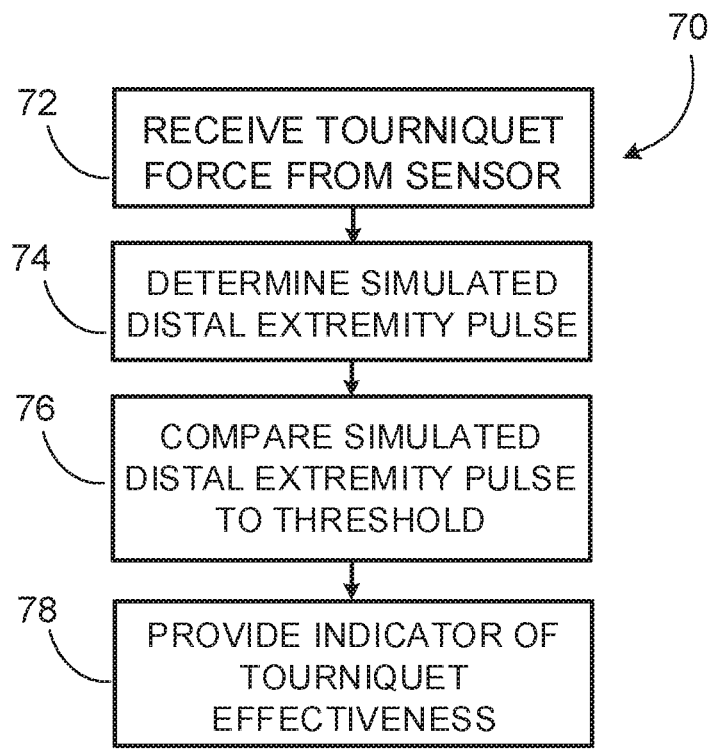
FIG. 4 is a method of operating a tourniquet training device in accordance with some embodiments provided herein.

Referring to FIG. 4, a method 70 of operating tourniquet training device 10 or the tourniquet training device 40, via a non-transitory computer readable medium, processor, or microprocessor is shown. Tourniquet force data can be received from sensor(s) 20 or sensor(s) 32 at 72. Tourniquet force data can be raw data collected or can be data that has been modified to convert the data into force data (e.g., converting flow data into force data based on tube rigidity and flow rate). A simulated distal extremity pulse can be determined at 74. Simulated distal extremity pulse can be determined based on tourniquet force data. In some cases, simulated distal extremity pulse can be determined based on configurations of sensor(s) 20 or sensor(s) 32. For example, in some cases, different forces applied can result in the same simulated distal extremity pulse (e.g., representative of different patients with different characteristics). For example, when simulating a child, a first force may cause a first simulated distal extremity pulse; however, when simulating an adult, a second force, greater than the first force, may be needed to cause the first simulated distal extremity pulse. Simulated distal extremity pulse can be compared to a threshold at 76. In some cases, simulated distal extremity pulse can be compared to a range, or a plurality of thresholds. In some cases, the threshold can be representative of effective tourniquet application. In some cases, multiple thresholds, or ranges, can be used to distinguish between too little force, adequate force, and too much force. An indicator of tourniquet effectiveness can be provided at 78. The indicator of tourniquet effectiveness can be provided via indicator 26, which can be located on extremity cuff 22, a mobile device, or a combination thereof.

While this specification contains many specific implementation details, these should not be construed as limitations on the scope of any embodiment of the design or of what can be claimed, but rather as descriptions of features that can be specific to particular embodiments of particular designs. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described herein as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system modules and components in the embodiments described herein should not be understood as requiring such separation in all cases, and it should be understood that the described program components and systems can generally be integrated together in a single product or packaged into multiple products.

Particular aspects of the subject matter have been described. Other aspects are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing can be advantageous.

What is claimed is:

1. A tourniquet training device, wherein said tourniquet training device comprises:
    a sleeve defining an inner lumen configured to receive an arm or leg of a human; and
    an external compressible member at least partially surrounding an exterior of said sleeve,
    wherein pressure applied to said external compressible member via a tourniquet in an amount that reduces blood flow of a comparable arm or leg in the absence of said tourniquet training device does not reduce blood flow when said arm or leg is positioned within said sleeve.

2. The device of claim 1, wherein said tourniquet training device comprises a sensor embedded in said external compressible member.

3. The device of claim 2, wherein said sensor is a force sensor.

4. The device of claim 2, wherein said tourniquet training device comprises an indicator configured to indicate a tourniquet effectiveness based on data received from said sensor.

5. The device of claim 4, wherein said indicator is a light, a sound, a vibration, or a display.

6. The device of claim 2, wherein said tourniquet training device comprises a tube coupled to a fluid flow device, wherein said tube and said fluid flow device are embedded within said external compressible member.

7. The device of claim 6, wherein said tube is filled with a fluid, and wherein said sensor is coupled to said tube.

8. The device of claim 6, wherein said tube is removable from said external compressible member.

9. The device of claim 2, wherein said sensor is a flow sensor or a pressure sensor.

10. The device of claim 1, wherein said sleeve is rigid.

11. The device of claim 1, wherein said tourniquet training device comprises an internal compressible member located within said sleeve, wherein said internal compressible member is located between said sleeve and said arm or leg when said arm or leg are positioned within said sleeve.

12. The device of claim 11, wherein said internal compressible member is an air bladder.

13. The device of claim 1, wherein pressure applied to said external compressible member via a tourniquet in an amount that stops blood flow of a comparable arm or leg in the absence of said tourniquet training device does not stop blood flow when said arm or leg is positioned within said sleeve.

14. A method of using a tourniquet training device, wherein said tourniquet training device comprises a sleeve defining an inner lumen configured to receive an arm or leg of a human, an external compressible member at least partially surrounding an exterior of said sleeve, and a sensor for measuring pressure applied to said external compressible member, wherein said method comprises:
    positioning said arm or said leg within said inner lumen;
    applying pressure via a tourniquet to said external compressible member; and
    receiving a first indication of tourniquet effectiveness from said tourniquet training device or a device in communication with said tourniquet training device,
    wherein said first indication of tourniquet effectiveness is based on force data obtained from said sensor, and
    wherein said tourniquet training device comprises a tube coupled to a fluid flow device, wherein said tube and said fluid flow device are embedded within said external compressible member.

15. The method of claim 14, wherein pressure applied to said external compressible member via said tourniquet in an amount that reduces blood flow of a comparable arm or leg in the absence of said tourniquet training device does not reduce blood flow when said arm or leg is positioned within said sleeve.

16. The method of claim 14, wherein said sensor is a force sensor.

17. The method of claim 14, wherein said tourniquet training device comprises an indicator configured to indicate a tourniquet effectiveness based on data received from said sensor.

18. The method of claim 17, wherein said indicator is a light, a sound, a vibration, or a display.

19. The method of claim 17, wherein said method comprises receiving a second indication of tourniquet effectiveness via said indicator.

20. The method of claim 14, wherein said tube is filled with a fluid, and wherein said sensor is coupled to said tube.

21. The method of claim 14, wherein said sensor is a flow sensor or a pressure sensor.

22. The method of claim 14, wherein said tube is removable from said external compressible member.

23. The method of claim 14, wherein said tourniquet training device comprises an internal compressible member located within said sleeve, wherein said internal compressible member is located between said sleeve and said arm or leg when said arm or leg are positioned within said sleeve.

24. The method claim 23, wherein said internal compressible member is an air bladder.

25. The method of claim 14, wherein said method comprises adjusting the pressure of said tourniquet based on said first indication of tourniquet effectiveness.

26. The method of claim 14, wherein pressure applied to said external compressible member via said tourniquet in an amount that stops blood flow of a comparable arm or leg in the absence of said tourniquet training device does not stop blood flow when said arm or leg is positioned within said sleeve.

27. A method of using a tourniquet training device, wherein said tourniquet training device comprises a sleeve defining an inner lumen configured to receive an arm or leg of a human, an external compressible member at least partially surrounding an exterior of said sleeve, and a sensor for measuring pressure applied to said external compressible member, wherein said method comprises:
- positioning said arm or said leg within said inner lumen;
- applying pressure via a tourniquet to said external compressible member; and
- receiving a first indication of tourniquet effectiveness from said tourniquet training device or a device in communication with said tourniquet training device,
- wherein said first indication of tourniquet effectiveness is based on force data obtained from said sensor, and
- wherein said sleeve is rigid.

\* \* \* \* \*

UNITED STATES PATENT AND TRADEMARK OFFICE
CERTIFICATE OF CORRECTION

| | |
|---|---|
| PATENT NO. | : 11,672,544 B2 |
| APPLICATION NO. | : 16/636408 |
| DATED | : June 13, 2023 |
| INVENTOR(S) | : M. Susan Hallbeck et al. |

It is certified that error appears in the above-identified patent and that said Letters Patent is hereby corrected as shown below:

In the Claims

In Column 12, Line 54, In Claim 24, after method insert -- of --.

Signed and Sealed this
Nineteenth Day of November, 2024

Katherine Kelly Vidal
*Director of the United States Patent and Trademark Office*